US00PP34234P2

(12) United States Plant Patent
Carruth

(10) Patent No.: US PP34,234 P2
(45) Date of Patent: May 17, 2022

(54) ***FLORIBUNDA* ROSE PLANT NAMED 'WEKCASPETONO'**

(50) Latin Name: *Rosa hybrida*
Varietal Denomination: WEKcaspetono

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/300,885

(22) Filed: Dec. 7, 2021

(51) Int. Cl.
*A01H 5/02* (2018.01)
*A01H 6/74* (2018.01)

(52) U.S. Cl.
USPC ..... Plt./146
CPC ..... *A01H 6/749* (2018.05)

(58) Field of Classification Search
USPC ..... Plt./146
CPC ..... A01H 6/749; A01H 5/02
See application file for complete search history.

(56) References Cited

U.S. PATENT DOCUMENTS

PP16,250 P2 2/2006 Zary

OTHER PUBLICATIONS

Rose (Rosa 'Candy Spelling') in the Roses Database, Garden.org, https://garden.org/plants/view/645375/Rose-Rosa-Candy-Spelling/, 3 pages, last visited Dec. 17, 2021.
ROSE (Rosa 'Dr. Huey') in the Roses Database, Garden.org., https://garden.org/plants/view/1545/Rose-Rosa-Dr-Huey/, 9 pages, last visited Dec. 15, 2021.
Prior Product Sales, 3 pages Mar. 8, 2021.
Rose (Rosa 'Top Notch') in the Roses Database, Garden.org., https://garden.org/plants/view/161/Rose-Rosa-Top-Notch/, 5 pages, last visited Dec. 17, 2021.
Weeks Roses Wholesale Rose Catalog, "Forever Amber", 13 pages 2022.

*Primary Examiner* — Keith O. Robinson
(74) *Attorney, Agent, or Firm* — McKee, Voorhees & Sease, PLC

(57) ABSTRACT

A new variety of Floribunda rose suitable for garden decoration, having flowers of apricot coloration.

1 Drawing Sheet

Classification: The present invention relates to a new *Rosa hybrida* plant.

Variety denomination: The new plant has the varietal denomination 'WEKcaspetono'.

BACKGROUND OF THE INVENTION

This invention relates to a new and distinct variety of Floribunda Rose. It has as its seed parent the variety known as 'WEKcibamcala' (not patented) and as its pollen parent the variety known as 'MACamster' (not patented).

SUMMARY OF THE INVENTION

Among the features which distinguish the new variety from other presently available and commercial rose cultivars known to the inventor are the following combinations of characteristics: its elegant old-fashioned apricot flower, its excellent color stability throughout the life of the flower and its abundant blooms. The plant has an upright bushy somewhat spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKcaspetono' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKcibamcala' by the following combination of characteristics: whereas 'WEKcaspetono' bears flowers of apricot coloration with a moderate fruity fragrance, 'WEKcibamcala' bears flowers of orange-pink blended coloration with lighter reverse and with mild fragrance. The new variety has an upright bushy somewhat spreading medium height growing habit (about 82 to about 150 cm. in height), whereas the seed parent has a bushy rounded moderately spreading shorter growing habit (about 80 to about 100 cm. in height).

The new variety may be distinguished from its pollen parent, 'MACamster' by the following combination of characteristics: whereas 'WEKcaspetono' bears very double flowers (about 44 to 104 petals) of apricot coloration, 'MACamster' bears double flowers of golden-apricot coloration with significantly lesser petalage (about 26 to 40 petals). The new variety has a moderate fruity fragrance, whereas the pollen parent has a strong fruity to musk fragrance.

COMPARISON WITH THE CLOSEST COMMERCIALLY AVAILABLE CULTIVAR

The new variety may be distinguished from its closest commercially available cultivar, 'JACarque' (U.S. Plant Pat.

No. 16,250) by the following combination of characteristics: whereas 'WEKcaspetono' bears very double (about 44 to 104 petals) medium sized flowers (about 7.7 to about 10.8 cm. in diameter), 'JACarque' bears double larger flowers (about 10.0 to about 12.0 cm. in diameter) with significantly lesser petalage (about 30 to 35 petals). The new variety has a moderate fruity fragrance, the closest commercially available cultivar has a strong, sweet honey fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3- to 4-year-old rose plants of the new variety grown outdoors in Wasco, Calif. in the month of November. Throughout this specification, color references and/or values are based upon The Colour Chart of The Royal Horticultural Society (2001) except where common terms of color definition are employed.

DESCRIPTION OF THE NEW VARIETY

The following description is of 3- to 4-year-old rose plants of the new variety grown outdoors in Wasco, Calif. in the month of November. Phenotypic expression may vary with environmental, cultural, and climatic conditions, as well as differences in conditions of light and soil.

FLOWER

The new variety usually bears its flowers singly. Flowers are borne on strong short to medium length stems (about 18 to about 28 cm.). Outdoors, the plant blooms abundantly and nearly continuously during the growing season. The flowers have a moderate fruity fragrance.

BUD

The peduncle is about 1.4 to about 2.9 cm. in length, of average caliper (about 0.2 to about 0.4 cm. in diameter), and erect. It is slightly rough, with numerous stipitate glands. Peduncle color is near 146C sometimes suffused, especially on the side exposed to the sun, with near 183C.

Before the calyx breaks, the bud is about 1.2 to about 2.2 cm. in diameter at the widest point, about 1.7 to about 2.4 cm. in length, and pointed to ovoid in shape. The surface of the bud bears between 1 to 5 foliaceous appendages, usually with slender foliaceous parts extending beyond the tip of the bud about ¼ of its length. Bud color is near 26C often heavily suffused, especially on the side exposed to the sun, with between 39B and 39A. Occasionally there are dark patches of 53A.

The sepals are 5 to as many as 8 per flower, about 1.8 to about 2.8 cm. in length and about 0.6 to about 1.2 cm. in width at the widest point. The outer surface color of the sepal is near 26C often heavily suffused, especially on the side exposed to the sun, with between 39B and 39A. Occasionally there are dark patches of 53A. The outer surface of the sepal is somewhat smooth and bears between 0 to 5 foliaceous appendages with many hairs and few stipitate glands. The inner surface color of the sepal is near 147B broadly bordered by near 155D. After the sepals open, the inner surface color is sometimes lightly suffused, especially on the area exposed to the sun, with between 183C and 183D. The inner surface of the sepal is covered with fine wooly tomentum; sepal margins are entire and lined with few stipitate glands and many hairs. The sepals are moderately permanent, usually straight to spear-shaped in shape with acute apices.

The receptacle of the flower is of somewhat short to medium length (about 0.4 to about 1.1 cm.) and of moderately small to medium sized caliper (about 0.5 to about 1.2 cm. in diameter). The receptacle is funnel shaped in form. Its surface is smooth with thick fleshy walls. The receptacle color is between 137C and 137D.

As the petals open (after the calyx breaks), the bud is about 2.0 to about 2.6 cm. in diameter at the widest point, about 2.2 to about 3.1 cm. in length, and pointed to ovoid in form. The color of the under surfaces of the newly opened petals is between 29C and 29D. At the point where the petal attaches, there is a large zone of between 12C and 12B. The color of the upper surfaces of the newly opened petals is between 29C and 29D. At the point where the petal attaches, there is a large zone of between 12C and 12B.

BLOOM

When fully open, the bloom ranges from about 7.7 to about 10.8 cm. in diameter. Petalage is very double with about 44 to 104 petals and about 4 to 10 petaloids irregularly arranged. When partially open, the bloom form is globular, and the petals are spiraled with petal edges somewhat reflexed outward. When fully open, the bloom form is flattened and cupped, with petal edges somewhat reflexed outward.

PETALS

The substance of the petals is moderately heavy and of medium thickness, with upper surfaces somewhat shiny to satiny and under surfaces slightly satiny. The petals are about 3.2 to about 4.7 cm. in length and about 1.7 to about 4.3 cm. in width at the widest point. Petal margins are entire.

The outer petals are ovate to orbicular in shape with rounded apices and sometimes slightly notched with one to two notches.

The inner petals are ovate to obovate with rounded apices and sometimes slightly notched with one to two or more notches.

Petaloids are about 1.0 to about 2.0 cm. in length and about 0.5 to about 1.2 cm. in width at the widest point. Petaloids are oblong to spatulate shaped with rounded apices.

NEWLY OPENED FLOWER

The under and upper surface color of the outer, intermediate and inner petals is between 29C and 29D. At the point where the petal attaches, there is a large zone of between 12C and 12B.

The under and upper surface colors of the petaloids are similar in coloration to the upper and under surfaces of the intermediate and inner petals.

The general tonality of the newly opened flower is between 29C and 29D.

THREE-DAY-OLD FLOWER

The under and upper surface color of the outer, intermediate and inner petals is between 29C and 29D. At the point where the petal attaches, there is a large zone of between 12B and 12C.

The under and upper surface colors of the petaloids are similar in coloration to the upper and under surfaces of the intermediate and inner petals.

The general tonality of the three-day-old flower is between 29C and 29D.

On the spent bloom, the petals usually drop off cleanly.

In November in Wasco, Calif., blooms on the bush growing outdoors generally last about five to six days. Cut roses from plants grown outdoors and kept at normal indoor living temperatures generally last about five to six days.

MALE REPRODUCTIVE ORGANS

Stamens are many in number (average about 120) and are arranged regularly about the pistils; a few are mixed with petaloids. The filaments are of medium to long length (about 0.7 to about 0.8 cm.) most with anthers. Filaments are near 6C in color. The anthers are medium in size for the class and all open approximately at the same time. Anther color when immature is near 13C on the external part and near 13D on the internal part. Anther color at maturity is near 22B on the external part and near 20C on the internal part. Pollen is moderate to abundant and near 163A in color.

FEMALE REPRODUCTIVE ORGANS

Pistils vary in number (average about 80). The styles are somewhat even, average in length (about 0.7 to about 0.9 cm.), thin to average in caliper, and loosely bunched. Stigma color is near 161D. Style color is near 50D. Ovaries are all enclosed in the calyx. The ovaries are of small size and between 157B and 157C in color.

Hips have not been observed on this variety when grown in Wasco, Calif.

FOLIAGE

The compound leaves are usually comprised of three to five leaflets and are borne abundantly. The five-leaflet leaves are about 7.0 to about 14.0 cm. in length and about 4.5 to about 12.0 cm. in width at the widest point, moderately leathery to somewhat crisp in texture on both sides, and glossy in finish on the upper side and slightly shiny to matte in finish on the underside. The leaves have a pinnate venation pattern. The terminal leaflets are about 3.5 to about 8.0 cm. in length and about 2.0 to about 4.0 cm. in width at the widest point, shaped ovate with acute apices and moderately acute to obtuse bases. Their margins simply serrate.

The upper surface color of the mature leaf is near 139A. The under-surface color of the mature leaf is between 146B and 147B. The under and upper colors of the leaf veins on the mature leaf are similar in coloration to the upper and under surfaces colors of the mature leaf. The upper surface color of the young leaf is between N199A and N199B, sometimes lightly suffused with near 183A. The under-surface color of the young leaf is between 194A and 195A, sometimes lightly suffused with between 178A and 178B. The under and upper colors of the leaf veins on the young leaf are similar in coloration to the upper and under surfaces colors of the young leaf.

The rachis is about 3.0 to about 6.0 cm. in length, about 0.1 to about 0.2 cm in width at the widest point, and moderately rough. The upper side is moderately grooved with few hairs and stipitate glands on the edges of the grooves. The under-side of the rachis is moderately rough with few hairs, few stipitate glands and few small prickles. The rachis color is near 146B on the under-side and near 183A on the upper side, often moderately suffused on the young leaves with near 178A.

The stipules are about 0.6 to about 1.2 cm. in length and somewhat narrow to medium in width (about 0.3 to about 0.8 cm.) with medium to long straight points that usually turn out at an angle of more than 45 degrees and sometimes recurve toward the stem. The under and upper surface color of the stipule is near 146B. The upper and under surfaces of the stipules are smooth in texture.

The petiole is somewhat light in caliper and moderately rough. The upper side is moderately grooved with few hairs and stipitate glands on the edges of the grooves. The under-side of the petiole is moderately rough with few hairs, few stipitate glands and few small prickles. The petiole is about 0.7 to about 1.5 cm. in length and about 0.1 to about 0.2 cm in width at the widest point. The petiole color is near 146B on the under-side and near 183A on the upper side, often moderately suffused on the young leaves with near 178A.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, Calif. The plant's winter hardiness and drought/heat tolerance are yet to be determined.

GROWTH

The plant has an upright bushy somewhat spreading medium height growing habit (about 82 to about 150 cm. in height and about 86 to about 118 cm. spread at the widest point), with full branching. It displays moderately vigorous growth, and the canes are of medium to somewhat heavy caliper for the class (about 1.5 to about 2.6 cm. in diameter at the widest point).

The color of the major stems is between 146A and 146B. The major stems are rough in texture and they bear some large prickles that are about 0.5 to about 0.7 cm. in length. The large prickles are hooked slightly downward with a medium length oval base; prickle color is near 200D. The major stem bears few small prickles of similar shape and coloration.

The color of the branches is between 146A and 146B. The branches are rough in texture, and they bear some large prickles which are of similar size and shape to the large prickles on the major stems; prickle color is near 200D. The branches bear few small prickles of similar shape and coloration.

The color of the new shoots is between 178A to 178B rapidly turning to near 146C. The new shoots are rough in texture, and they bear some large prickles which are of similar size and shape to the large prickles on the major stems; prickle color is near 178B and rapidly turning to near 146D. The shoots bear few small prickles of similar shape and coloration.

I claim:

1. A new and distinct Floribunda rose plant of the variety designated 'WEKcaspetono' substantially as described and illustrated herein.

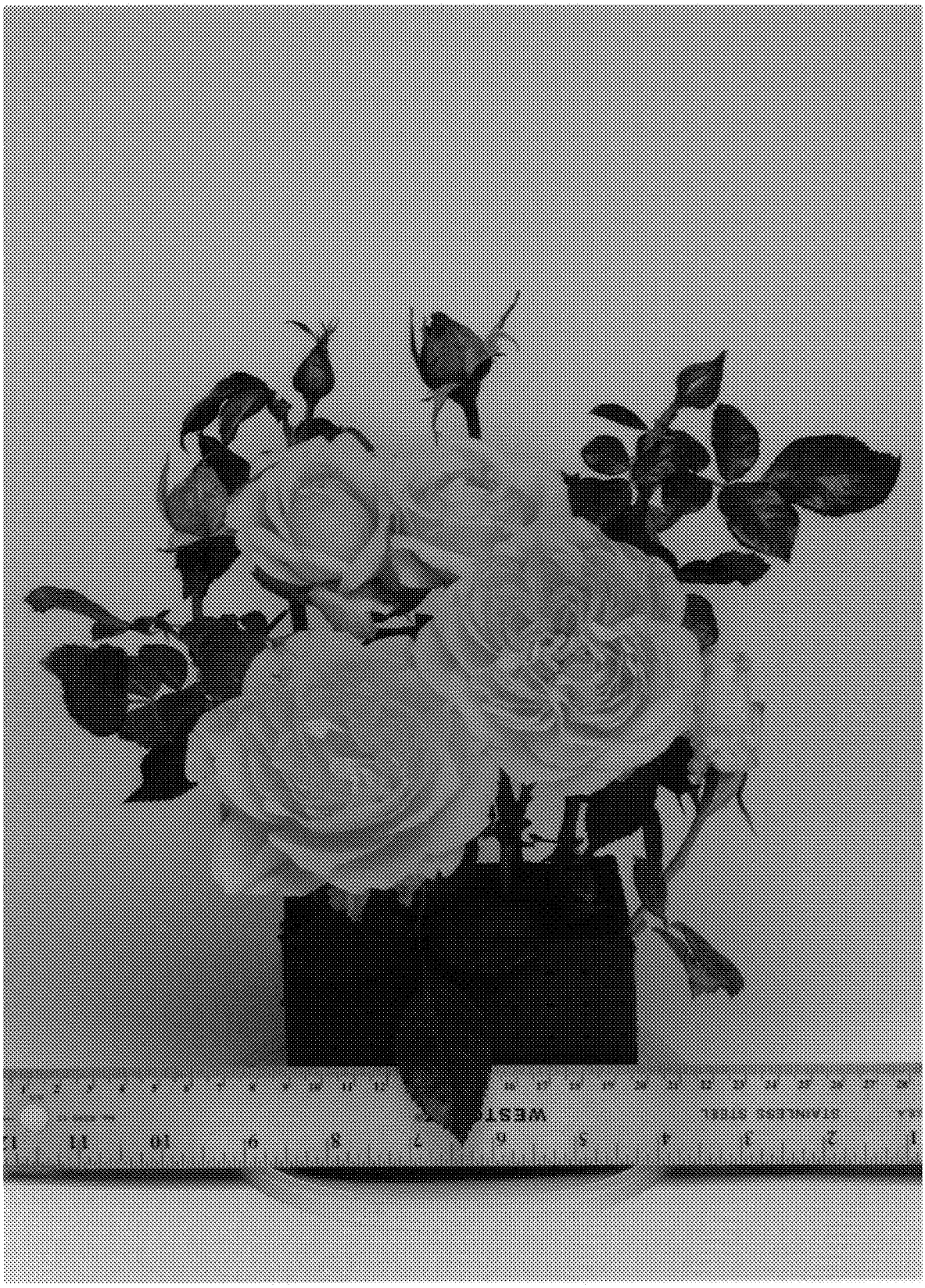

* * * * *